(12) United States Patent
Kornacki et al.

(10) Patent No.: US 9,029,156 B2
(45) Date of Patent: May 12, 2015

(54) MEASURING PROPERTIES AND AMOUNT OF PRODUCIBLE OIL IN SHALE-OIL RESERVOIR SAMPLES

(71) Applicant: Weatherford/Lamb, Inc., Houston, TX (US)

(72) Inventors: Alan S. Kornacki, Houston, TX (US); Patricia M. O'Neal, Houston, TX (US); Kathryn E. Washburn, Houston, TX (US); Kevin L. Kmiec, Houston, TX (US)

(73) Assignee: Weatherford Technology Holdings, LLC, Houston, TX (US)

( * ) Notice: Subject to any disclaimer, the term of this patent is extended or adjusted under 35 U.S.C. 154(b) by 85 days.

(21) Appl. No.: 13/890,932

(22) Filed: May 9, 2013

(65) Prior Publication Data

US 2014/0157870 A1 Jun. 12, 2014

Related U.S. Application Data

(60) Provisional application No. 61/644,844, filed on May 9, 2012.

(51) Int. Cl.
*G01N 33/24* (2006.01)
*G01N 33/28* (2006.01)

(52) U.S. Cl.
CPC .......... *G01N 33/2835* (2013.01); *G01N 33/241* (2013.01)

(58) Field of Classification Search
CPC .......................... G01N 33/2835; G01N 33/241

USPC ............................................ 436/25, 29, 31–32
See application file for complete search history.

(56) References Cited

U.S. PATENT DOCUMENTS

| | | | | |
|---|---|---|---|---|
| 2,095,056 | A | * | 10/1937 | Clough ........................... 422/82 |
| 2,733,135 | A | * | 1/1956 | Huckabay ........................ 436/31 |
| 3,887,331 | A | * | 6/1975 | Baldwin ........................ 436/31 |
| 4,029,568 | A | * | 6/1977 | Pittman et al. ................ 208/415 |
| 4,485,071 | A | | 11/1984 | Larter |
| 4,492,674 | A | * | 1/1985 | Schweighardt ............... 422/535 |

(Continued)

FOREIGN PATENT DOCUMENTS

FR 2958752 10/2011

OTHER PUBLICATIONS

Vogel Jr, A. W. et al, SPE publication 10884, 1982, 15 pages.*

(Continued)

*Primary Examiner* — Arlen Soderquist
(74) *Attorney, Agent, or Firm* — Wong, Cabello, Lutsch, Rutherford & Brucculeri LLP

(57) ABSTRACT

The subject matter of the present disclosure is directed to developing a method of measuring the amount of producible oil and the producible oil saturation in shale-oil reservoirs using sample source rock. Further, the physical and chemical properties and amounts of producible oil in shale-oil reservoir samples may be determined. First and second solvents are applied to a sample source rock to extract petroleum from the sample source rock. The extracted source rock, the twice-extracted source rock, and the first and second extracted petroleum may be analyzed to determine the characteristics and properties of the reservoir rock.

20 Claims, 9 Drawing Sheets

(56) References Cited

U.S. PATENT DOCUMENTS

| | | | | |
|---|---|---|---|---|
| 4,603,115 | A | * | 7/1986 | Schweighardt ............... 436/178 |
| 4,634,680 | A | * | 1/1987 | Kingsley ....................... 436/178 |
| 4,866,983 | A | * | 9/1989 | Vinegar et al. ............. 73/152.09 |
| 4,920,792 | A | * | 5/1990 | DiFoggio ................... 73/152.07 |
| 4,990,773 | A | * | 2/1991 | Supernaw et al. ............ 250/255 |
| 5,114,567 | A | * | 5/1992 | DiFoggio ...................... 208/401 |
| 5,174,966 | A | * | 12/1992 | Durand et al. ................ 422/534 |
| 5,181,428 | A | * | 1/1993 | Chriswell ................... 73/863.12 |
| 5,299,453 | A | * | 4/1994 | Sprunt et al. ............... 73/152.23 |
| 5,843,787 | A | * | 12/1998 | Trabelsi et al. ............... 436/139 |

OTHER PUBLICATIONS

Mueller, E. et al, Organic Geochemistry 1998, 28, 625-631.*
International Search Report and Written Opinion received in corresponding PCT Application No. PCT/US2013/040389, dated Oct. 14, 2013.
Muellera, et al. "Extraction of high molecular weight hydrocarbons from source rocks: An example from the Green River Formation, Uinta Basin, Utah," Organic Geochemistry, Pergamon, Amsterdam, NL, vol. 28, No. 9-10, Jun. 1, 1998, pp. 625-631, XP002611435, ISSN: 0146-6380, DOI: 10.1016/SO146-6380(98)00031-X.

* cited by examiner

MEASURING PROPERTIES AND AMOUNT OF PRODUCIBLE OIL IN SHALE-OIL RESERVOIR SAMPLES

This application claims the benefit of U.S. Provisional Application No. 61/644,844, filed May 9, 2011, which is incorporated herein in its entirety.

BACKGROUND

The search for, and evaluation of, unconventional reservoirs of hydrocarbons has become increasingly important in the global energy market. These unconventional reservoirs, such as shale-oil reservoirs, may include crude oil, kerogen, and bitumen. Kerogen, which ultimately generated the crude oil in the reservoir, contains organic compounds that are insoluble in organic solvents. Bitumen is a viscous intermediate hydrocarbon with properties in between those of crude oil and kerogen. Bitumen is often present in source rocks that have begun to generate oil. When these source rocks undergo catagenesis, the kerogen is cracked into smaller molecules to produce bitumen. Similarly, the bitumen may further crack into smaller molecules to produce crude oil.

Petroleum geochemists use the term extractable organic matter (EOM) to describe the petroleum that can be extracted from a thermally-mature oil-prone source rock using an organic solvent. EOM is a mixture of the crude oil generated and retained by the source rock, plus a heavier petroleum phase ("bitumen") that the kerogen also generated. Bitumen is enriched in non-hydrocarbon compounds that contain nitrogen, sulfur, and/or oxygen ("NSO" compounds) and asphaltenes. It subsequently cracks to lighter, less viscous producible crude oil. Bitumen probably is too viscous to be efficiently expelled from a source rock, although some oil-prone source rocks that contain sulfur-rich kerogen expel heavy tarry oil that may resemble bitumen. Some bitumen and producible oil also may be dissolved in—or sorbed on—kerogen. The kerogen may eventually expel producible oil (and possibly some bitumen) into adjacent intergranular porosity.

Because existing technologies to analyze core samples cannot discriminate between these types of hydrocarbons, there is not an effective way to estimate the quantity and quality of potentially recoverable hydrocarbons in these reservoirs. The analytical techniques petroleum engineers and geochemists currently use to measure the amount of oil in shale-oil reservoirs do not adequately distinguish between producible oil and bitumen. In the same way, the physical and chemical properties and value of the producible oil in a reservoir cannot be determined. Those properties may include API gravity and sulfur content. API gravity, defined by the American Petroleum Institute, is a measure for denoting the density of crude oil. It is an inverse measure; therefore, the lighter the crude, the higher the API gravity, and vice versa. Producible oil with a high API gravity and low sulfur content, which are both desirable characteristics for oil, may have a significantly different economic value from oil with a low API value and high sulfur content.

Core analysis procedures involve using an organic solvent (e.g., toluene) to extract all of the oil and bitumen in a core sample. Shale rock property (SRP) calculations of producible oil saturation (So) probably include the amount of producible oil and bitumen. Geochemists may use programmed pyrolysis to characterize source rocks by using a Source Rock Analyzer (SRA™) or by Rock Eval™. These involve the programmed temperature heating of a small sample of source rock in an inert atmosphere to volatilize or pyrolyze soluble and insoluble organic matter and measure the amount of HC compounds and carbon dioxide produced at different temperatures. These measurements can be used to estimate the amount of oil and residual kerogen in shale-oil samples. Producible oil may consist principally of distillable (S1) compounds, while bitumen and kerogen probably are more enriched in pyrolyzable (S2) compounds. However, producible oil and bitumen probably contribute to both pyrolysis peaks. Likewise, petrophysical log estimates and NMR laboratory measurements of producible oil saturation probably do not adequately resolve producible oil from non-producible bitumen or kerogen.

It is expensive to develop and manage shale-oil reservoirs. Accordingly, proper analysis and evaluation of shale-oil core samples can be of utmost importance in selecting locations and reservoirs to develop. The subject matter of the present disclosure is directed to overcoming, or at least reducing the effects of, one or more of the problems set forth above.

SUMMARY

The subject matter of the present disclosure is directed to developing a method of measuring the amount of producible oil and the producible oil saturation in shale-oil reservoirs using a core sample. Further, some of the physical and chemical properties of producible oil in shale-oil reservoir samples may be determined.

DETAILED DESCRIPTION

Figure 1A:
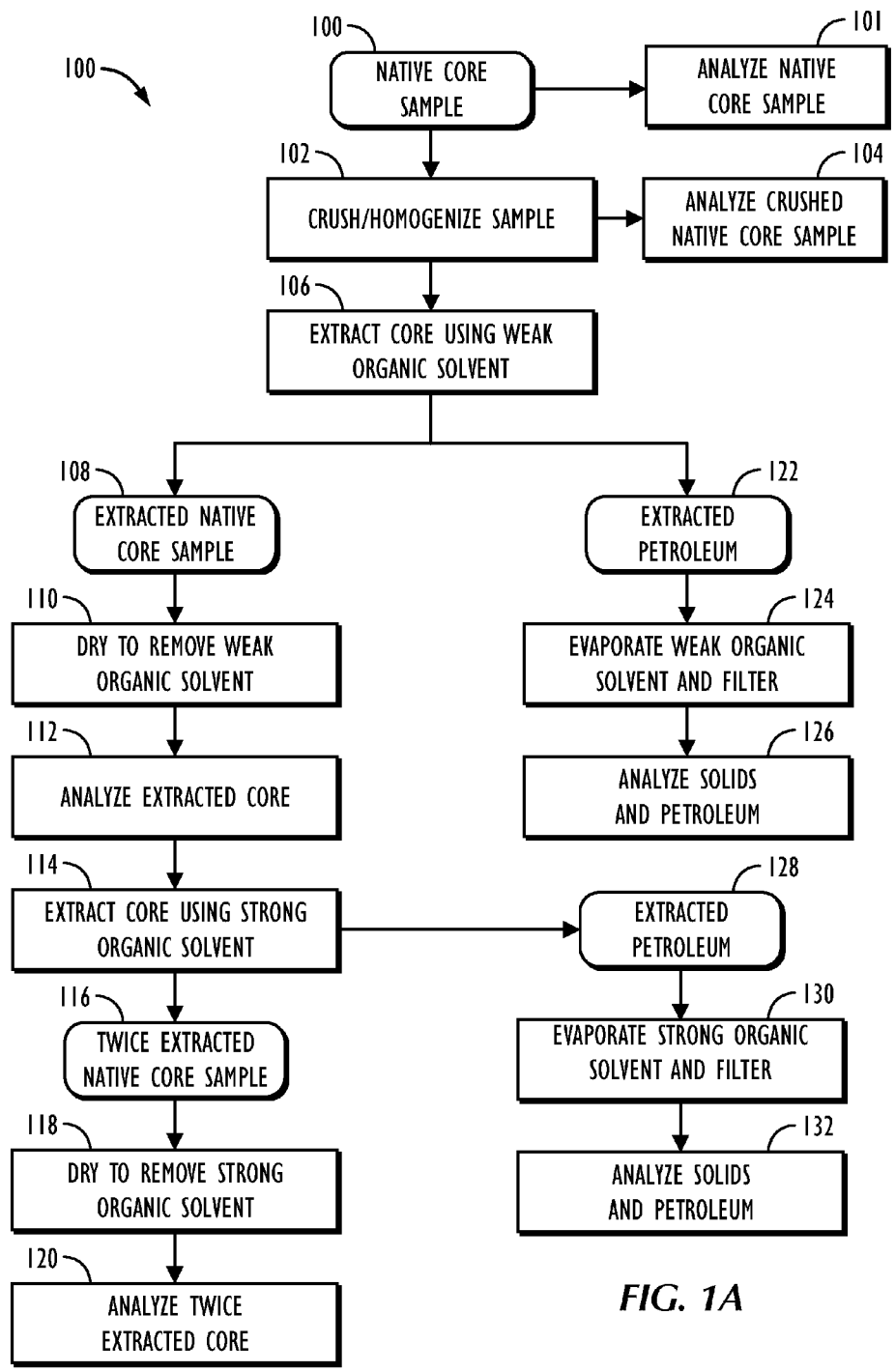
FIG. 1A illustrates the general workflow to analyze a native core sample to determine the amount and quality of producible oil it contains.

FIG. 1A illustrates the general workflow to analyze a native core from a shale-oil reservoir to determine the amount and quality of producible oil it contains. An intact piece of native core sample 100 may be analyzed (101). The native core sample 100 is crushed and homogenized (shown at 102), and further analysis may be performed on the crushed native core sample (104). The homogenization and analysis of the native core sample 100 will be described in further detail below with respect to FIG. 2.

At this point, a first organic solvent may be applied to the native core sample 100, as shown at 106. The first organic solvent may be a weak solvent, such as cyclohexane. The application of the cyclohexane will serve to divide the native core sample 100 into two substances, extracted petroleum 120 and extracted core 108. The cyclohexane solvent extracts petroleum from the native core sample 100 to form the extracted petroleum 122. Additionally, the remaining portion of the native core sample is referenced as extracted core 108. Both substances, the extracted petroleum 120 and the extracted native core sample 108, will contain the cyclohexane or other mild solvent. Before further analysis of either substance, the solvent should be adequately removed.

This extracted petroleum 122, which is in liquid form, may be evaporated and filtered to remove the cyclohexane or other solvent, as shown at 124, and the remaining evaporated petroleum may be analyzed, as shown at 126, for its representative chemical and physical properties. Any solids resulting from the filtration may be analyzed as well.

The remaining portion of native core sample 100, which is depleted of some hydrocarbons (i.e., the extracted petroleum 122), will form the extracted core sample 108. The extracted native core sample 108, which is a solid, may be dried (110) to remove the weak organic solvent. The resulting dried extracted native core sample may be analyzed as well, as shown at 112.

After the analysis of the extracted and dried native core sample has been performed, a second, stronger organic solvent may be applied to the extracted core sample. Some examples of the second solvent may be toluene or a mixture of solvents such as chloroform/methanol. This second solvent is applied at 114, and, once again, two substances are formed— the second solvent-extracted petroleum 128 and the twice extracted core 118.

The second solvent-extracted petroleum 128 is also evaporated, as shown at 130, to remove the second solvent. The evaporated petroleum may be filtered to separate solids from the petroleum. Any resulting solids and the petroleum may be analyzed, as shown at 132.

Returning to the twice extracted core 116, the twice extracted core may be dried to remove the second solvent, as shown at 118, and be further analyzed, as shown at 120.

At this stage, there are several substances at various phases of processing which should be retained for further comparative analysis. The substances include the native core sample 100, the extracted core sample 108, the twice extracted core sample 116, the petroleum 122 extracted from the first solvent, and the petroleum 128 extracted from the second solvent. As noted above, the petroleum extracted from the second solvent may be separated in the form of solids and filtrate.

As noted, FIG. 1A represents a general workflow for processing and evaluating a native core sample 100. This workflow may be modified or changed based on various factors, such as the success of applied analysis or based on the type, geographic origin, or other characteristics of the native core samples. For example, in some circumstances, it may be desirable to employ a third solvent to remove additional petroleum from the twice extracted native core sample.

Figure 1B:
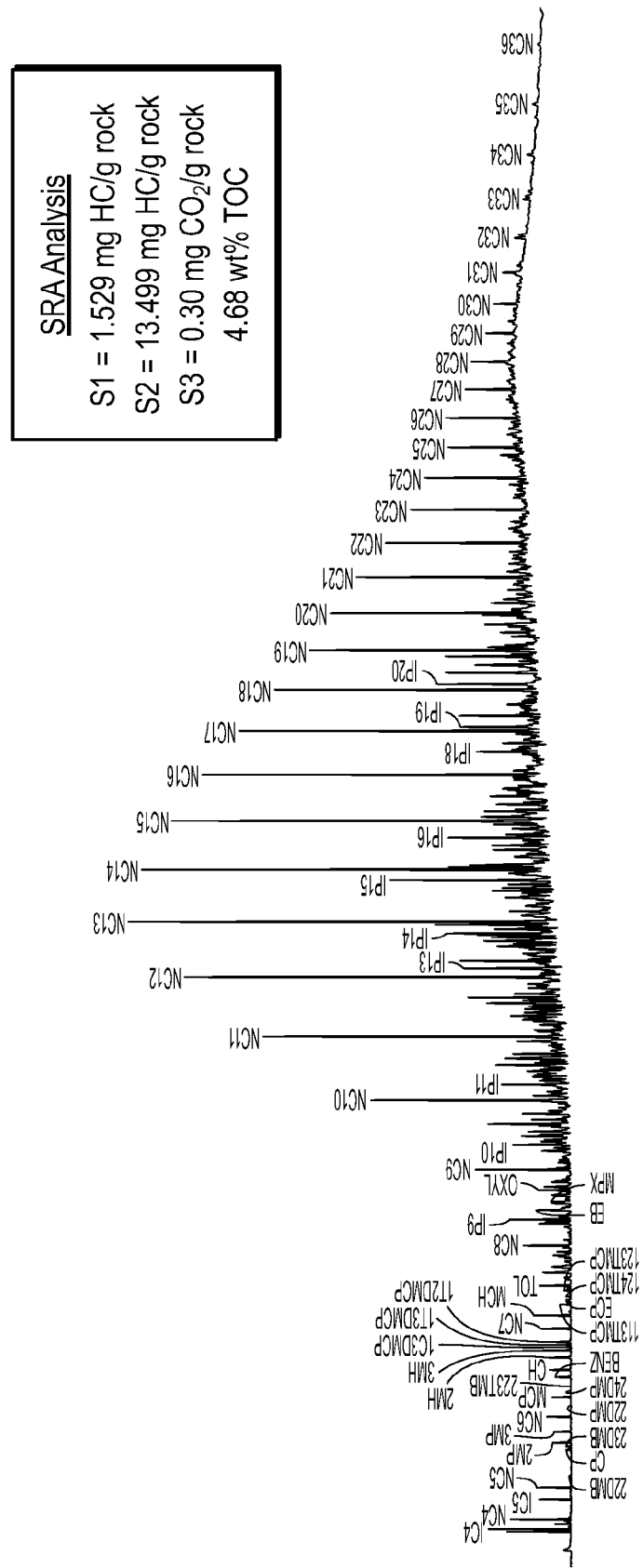
FIGS. 1B and 1C illustrate thermal extraction gas chromatographs and SRA analyses of native core sample 100 before and after extracting it using a weak organic solvent.
Figure 1C:
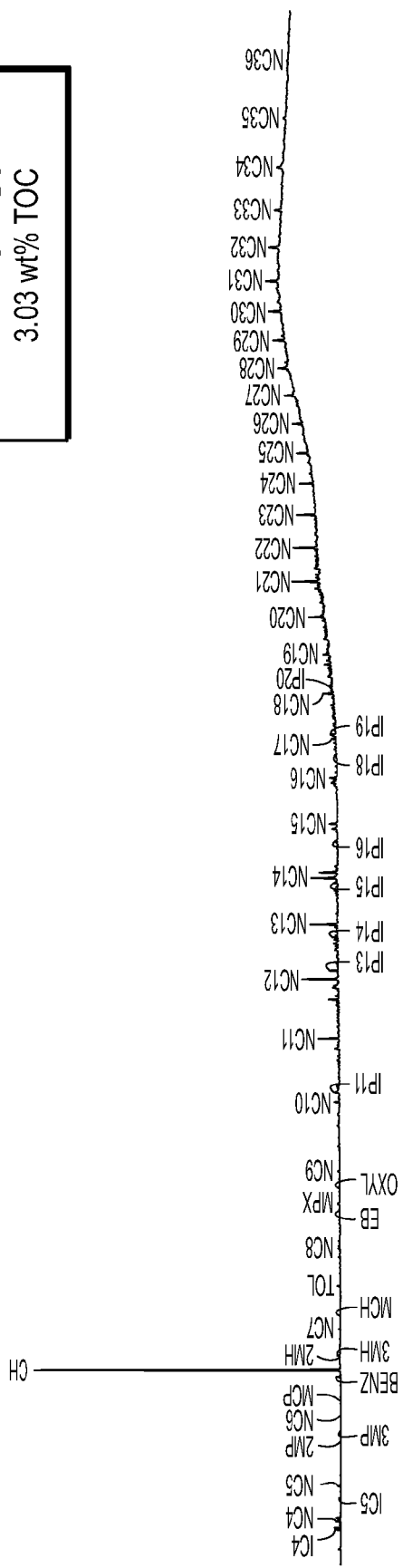

Sample test results of the native core sample 100 before and after extraction using cyclohexane are shown in FIGS. 1B-1C. FIG. 1B illustrates a thermal extraction gas chromatograph (TEGC) and SRA analysis of native core sample 100 before any extraction has been performed. FIG. 1C illustrates a TEGC and SRA analysis after the sample has been extracted with a weak organic solvent (here, cyclohexane) for 40 hours (i.e., extracted core sample 108). The SRA analysis demonstrates that the S1 (i.e., distillable HC compounds) is diminished with respect to that of FIG. 1B, indicating that extracted petroleum 122 was removed by the cyclohexane. The peak in the TEGC of FIG. 1C indicates that some solvent has been retained in the extracted core sample 108.

Figure 1D:
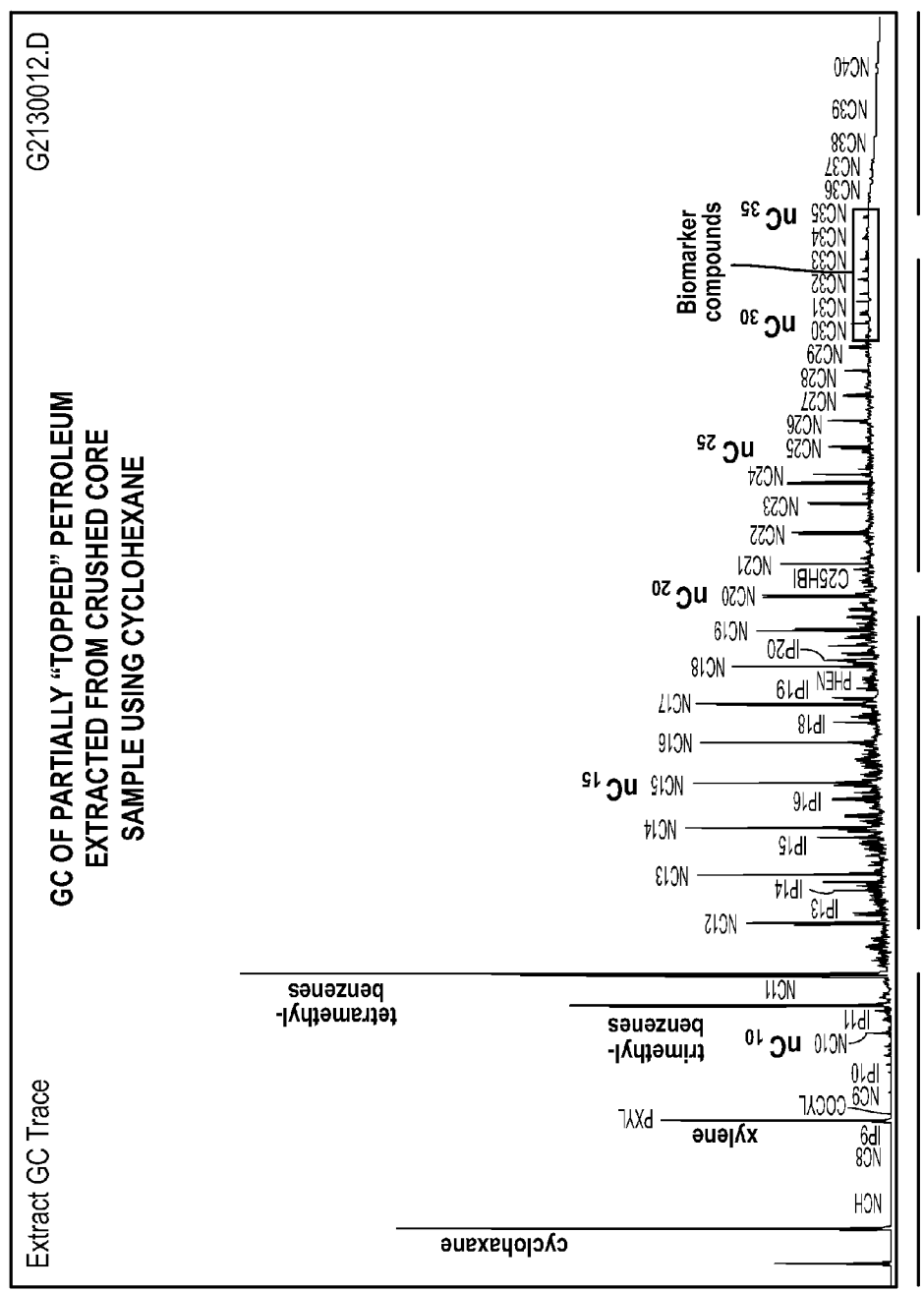
FIGS. 1D, 1E, and 1F illustrate gas chromatographs of petroleum extracted from the native core sample after extracting it sequentially with cyclohexane, toluene, and chloroform/methanol mixture, respectively.
Figure 1E:
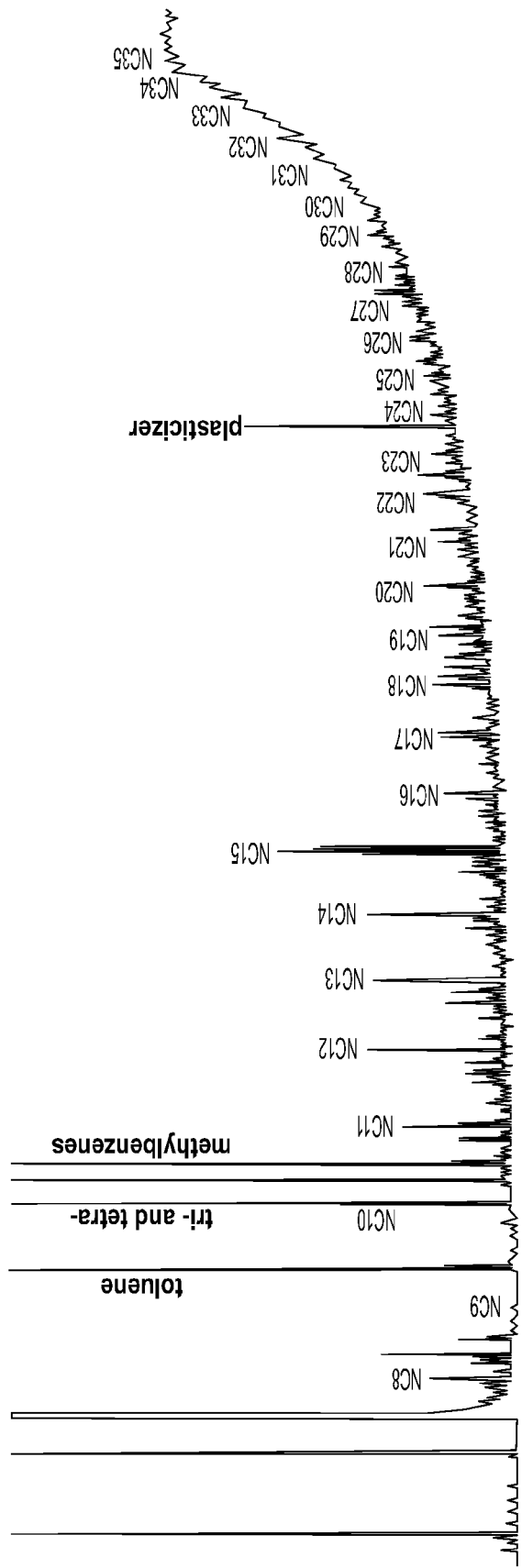
Figure 1F:
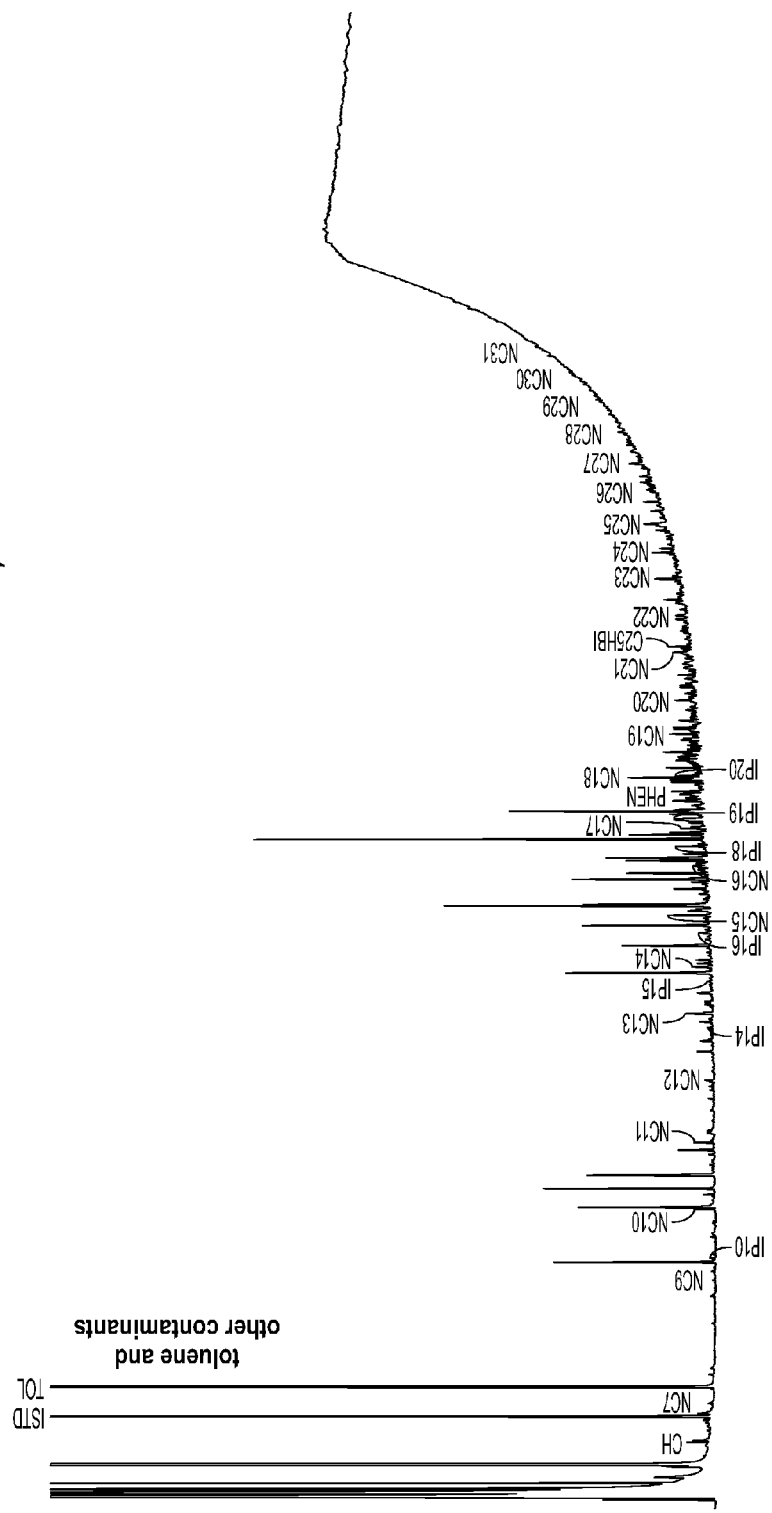

Sample test results of the petroleum extracted from the crushed native core sample 100 using various solvents are shown in FIGS. 1D-1F. FIG. 1D illustrates a gas chromatograph (GC) of a topped petroleum—one in which solvent has been evaporated—extracted from the crushed native core sample 100 using cyclohexane (i.e., extracted petroleum 122). FIG. 1E illustrates a magnified GC of petroleum extracted from the extracted native core sample 108 using toluene (i.e., second solvent-extracted petroleum 128). As noted above, a third solvent may also be applied to the twice extracted native core sample 116. FIG. 1F illustrates a magnified GC of a petroleum extracted from the native core sample which has been extracted using chloroform methanol, after having previously been extracted by cyclohexane and toluene (not shown in FIG. 1A).

The workflow is divided and described in further detail below. The analysis 102 and homogenization 102 of the native core sample are described with respect to FIG. 2. Additional detail regarding the extraction using the weak and strong solvents, the drying process of the extracted cores, and the analysis of the extracted source rock is shown and described with respect to FIG. 3.

Analysis the Native Core Samples

Figure 2:
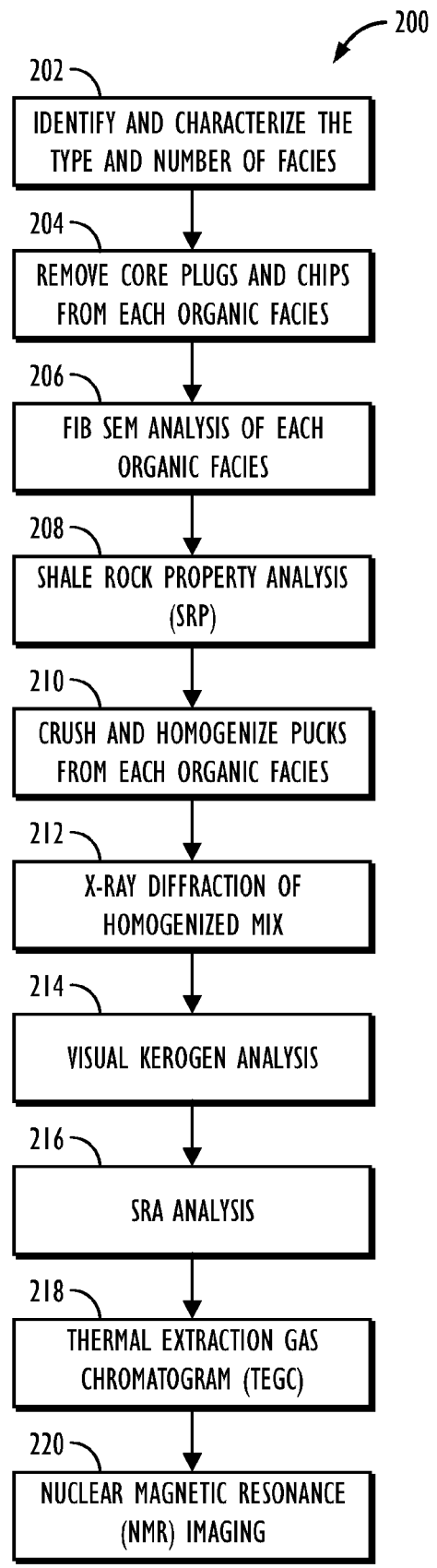
FIG. 2 illustrates a method for the initial analysis and preparation of the native core sample 100.

FIG. 2 illustrates method 200 for the initial analysis and preparation of the native core sample 100. At 202, the native core sample 100 is first examined to identify and characterize the type and number of organic facies (i.e., types of kerogen) present in that core using geochemical data obtained on representative rock chips from the native core sample 100. Several core plugs and core chips should be removed from each of the organic facies of the native core sample 100, as shown at 204. A thin section from a core plug is removed and analyzed to describe the mineralogy, fabric, and texture of the shale reservoirs. The distribution of minerals, kerogen, bitumen, crude oil, and porosity in a core chip should be determined from each organic facies by studying them using a focused ion beam scanning electron microscope (FIB SEM) device, as shown at 206. Additional data analysis of the native core may be obtained by performing a Shale Rock Property (SRP) analysis (210) to measure its porosity, permeability, bulk density, oil saturation, gas saturation, and water saturation of the native core sample 100.

After this initial analysis is performed, pucks of the native core sample 100 are selected such that there are pucks from each organic facies. A large enough sample size should be selected such that there is adequate source material for the subsequent analyses. For example, enough pucks from each organic facies may be selected to supply approximately 1000 grams of rock. At 210, these pucks may then be crushed and homogenized, as also referenced in FIG. 1A at 102, to be able to acquire data on the homogenized sample. At 212, X-ray diffraction may be used to determine the mineralogy of the crushed and homogenized core pucks. The amount of kerogen (wt % total organic carbon, or wt % TOC), the type of kerogen, and the level of thermal maturity may be characterized in an aliquot of the crushed and homogenized native core. The type of kerogen may be determined through a visual kerogen analysis (214) and through interpretation of data acquired from an SRA analysis, as shown at 216. The level of thermal maturity of the native core sample 100 may be determined by measuring vitrinite reflectance values and interpreting SRA data. Additional data analysis the native core may be obtained by performing a Shale Rock Property (SRP) analysis (210) to measure its porosity, permeability, bulk density, oil saturation, gas saturation, and water saturation of the native core sample 100. At 218, a thermal extraction gas chromatogram (TEGC) on the crushed and homogenized native core sample 100 may be obtained to characterize the type of crude oil it contains. Further, as shown at 220, a nuclear magnetic resonance (NMR) analysis may be performed on the native core sample to measure the T1 and T2 relaxation times of the kerogen, bitumen, crude oil, and clay-bound water in each sample. Performing these tests establishes a baseline set of data on the original native core sample 100.

Figure 3:
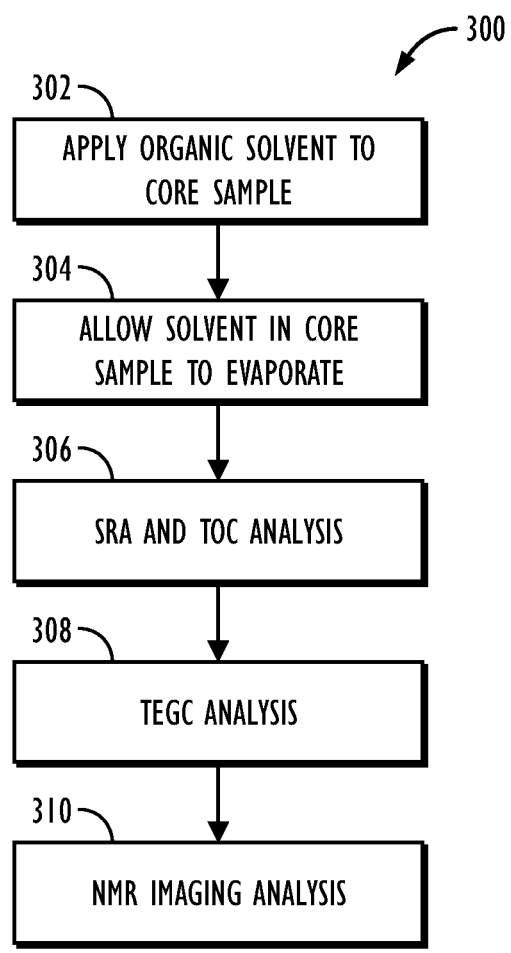
FIG. 3 illustrates a method for extraction using weak and strong organic solvents, the drying process of the extracted cores, and the analysis of the extracted core sample.

Referring now to FIG. 3, method 300 illustrates extraction using the weak and strong solvents, the drying process of the extracted cores, and the analysis of the extracted source rock. The method of FIG. 3 is first described in the context of using the weak organic solvent. At 302, the weak organic solvent, such as cyclohexane, may be used to extract petroleum from samples of the crushed and homogenized native core sample 100. As noted during the discussion of FIG. 1A, the application of the weak solvent forms two substances: extracted native core sample 108 and extracted petroleum 120. Because the extracted native core sample 108 may retain some of the organic solvent, the weak organic solvent should be allowed to evaporate, as shown at 304, so the solvent does not significantly contaminate the extracted native core sample 108. The evaporation may be performed with or without additional heating. The extracted native core sample 108 may be analyzed using the sequence of tests described above. At 306, SRA and TOC data may be obtained from the dried extracted native core sample 108. Further, at 308, a TEGC analysis on the extracted native core sample 108 may be performed to characterize the type of petroleum that remains in the extracted native core sample 108. Additionally, an NMR analysis of the extracted native core sample 108 may be performed to measure the T1 and T2 relaxation times of the kerogen, bitumen, crude oil, and/or clay-bound water remaining in the sample. Currently obtained NMR data measured on core samples from various shale-oil reservoirs indicate that the kerogen, bitumen, crude oil, and clay-bound water each may exhibit different and identifiable T1 and T2 relaxation times.

After the application and drying of the weak organic solvent, a strong organic solvent, such as toluene or chloroform methanol, may be applied to the extracted native core sample 108. Again, the method 300 of FIG. 3 may be performed. The strong organic solvent extracts relatively insoluble petroleum that may be enriched in bitumen from the extracted native core sample 108. As described above, the application of the strong organic solvent helps to separate the extracted native core sample 108 into the twice extracted native core sample 118 and the extracted petroleum 126. The twice extracted native core sample 118 may be heated and dried to evaporate the strong organic solvent. Similar to the tests described above, SRA and TOC data may be obtained on the twice extracted native core sample 118. Additionally, the petroleum contained in the twice extracted native core sample 118 may be analyzed using a TEGC analysis. The NMR analysis to determine the relaxation times of the various components of the twice extracted native core sample 118 should also be performed.

In parallel to these applications of weak and strong organic solvents to the crushed and homogenized native core sample, analysis may be performed on the original core chips that represented each of the various organic facies that were taken original core sample. Accordingly, the weak organic solvent may be used to extract petroleum from the core chips representing each of the organic facies that previously were analyzed using the FIB SEM device. After the application of the weak organic solvent, the chips may be further analyzed using the FIB SEM device to determine the distribution of minerals, kerogen, bitumen, crude oil, and porosity in each extracted core chip from each organic facies. After the application of the weak organic solvent to the core chips, the strong organic solvent may also be applied to extract some of the remaining relatively insoluble petroleum from each core chip. At this point, the FIB SEM device may again be used to determine the distribution of minerals, kerogen, bitumen, crude oil, and porosity.

Analysis of Extracted Petroleum Samples and Crude Oil Samples

Analysis may be performed on each of the extracted petroleum samples from FIG. 1A. This includes the extracted petroleum 122 which is extracted by the weak organic solvent from the native core sample 100. Also included is second solvent-extracted petroleum 128, which is extracted from the extracted native core sample 108 by the strong organic solvent. As shown in 124 and 130, these petroleum samples may be heated in order to evaporate the solvents, a process also known as "topping" the samples. Each extract may be analyzed after being topped, as shown at 126 and 132, respectively. Ideally, the extracts and the crude oil samples should be topped or evaporated identically, or nearly identically.

Figure 4:
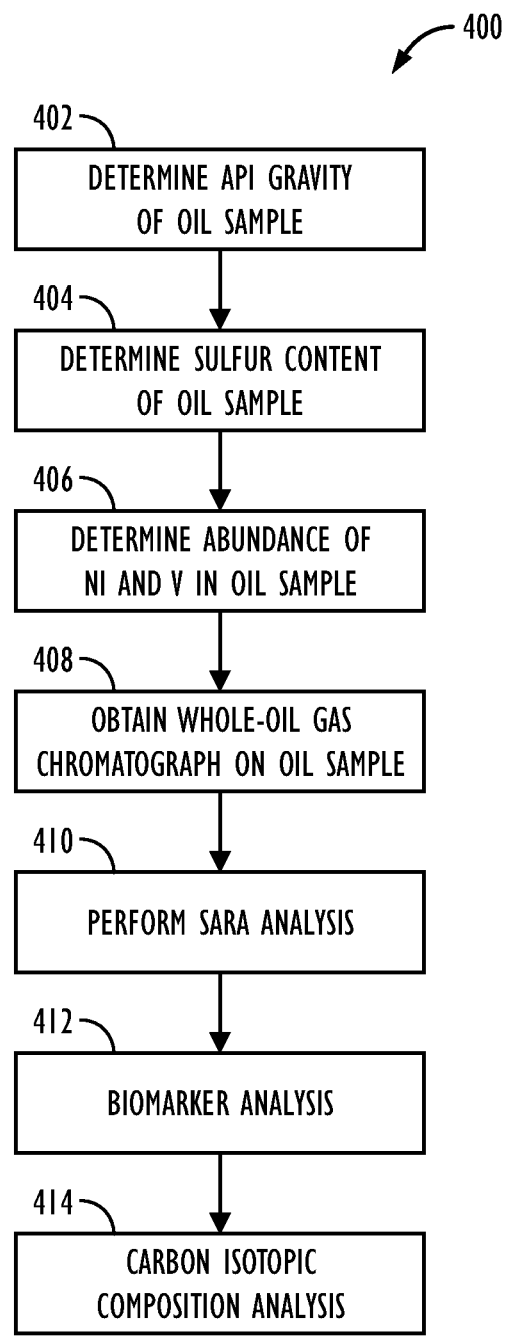
FIG. 4 illustrates the analysis that may be performed on the petroleum extracted from a core sample or a crude oil sample produced from the same shale-oil reservoir.

Method 400 in FIG. 4 illustrates this analysis. Analysis may include determining the API gravity (402), sulfur content (404), and abundance of nickel (Ni) and vanadium (V) (406). Further, a whole-oil gas chromatograph may be obtained on each petroleum extract (408). A SARA analysis, which determines saturates, aromatics, resins, and asphaltenes in a hydrocarbon sample, may also be performed (410). Further, carbon isotopic composition analysis (414) of the C15+ saturate and aromatic compounds and saturate and aromatic biomarker composition analysis may be performed (412).

One technical challenge regarding interpreting the data obtained from the native core samples and plugs is that the data from sample cores may be difficult to upscale to reservoir-scale volumes. This may be mitigated by identifying important lithofacies and kerogen organic facies and analyzing representative samples from each of the important facies. This is why the analysis of the native core chips, as discussed above, is important in addition to the analysis of the homogenized native core samples. Further challenges may be presented in the interpretation of the zones/facies from which crude oil samples are produced by nearby oil wells completed in the same shale-oil reservoir. This challenge may be mitigated by using oil fingerprinting technology on representative oil samples produced from the same area to reduce the uncertainty about the number and type of oils produced from the shale-oil reservoir.

To obtain a thorough fingerprinting analysis of the representative types of oils in each reservoir, crude oil samples produced from the same area and reservoir interval from which the shale-oil native core sample 100 was collected should be obtained. High-resolution gas chromatography data may be obtained on each of the oil samples. Further, hydrocarbon fingerprinting technology may be used to determine a measure of the similarity of the produced oil samples and the number of groups to which they can be classified. From these various crude oil samples from the shale reservoir, representative samples of each type of producible oil may be determined. This may be based on oil samples in each group that are so similar to each other that they can be considered representative of each type of producible oil present in the shale-oil reservoir.

From this point, each representative crude oil sample and samples of the representative crude oils that have been "topped" by evaporation and/or heating may be further analyzed to provide baseline data of the characteristics of the representative samples. The analysis may be the same as described with respect to FIG. 4 above. The API gravity and the sulfur content of the representative produced oil samples and "topped" oil samples may be determined. Additional tests checking for the presence and abundance of nickel, vanadium, or other critical elements in the crude oil samples and "topped" oil samples may be performed. Further, a complete gas chromatography analysis may be performed on each of the representative crude oil samples and "topped" oil samples. Obtaining this data for the representative crude oil samples and "topped" oil samples, as well as from the extracted petroleum described above, will enable a comparative analysis of the different representative samples with respect to the petroleum extracted from homogenized crushed core samples.

After performing the analyses of the samples above, there should be SRA data with respect to each of the following core samples and oils: 1) an aliquot of each crushed native core sample obtained from each organic facies (i.e., native core sample 100); 2) an aliquot of each crushed core sample from each organic facies after it has been extracted with a weak organic solvent (i.e., extracted native core sample 108); 3) an aliquot of each crushed core sample from each organic facies after it has been extracted with a weak organic solvent and a strong organic solvent (i.e., twice extracted native core sample 116); 4) the petroleum extracted from each crushed core using a weak organic solvent after that solvent has been removed by evaporating it (i.e., after evaporating extracted petroleum 122); 5) the petroleum extracted from each crushed core using a strong organic solvent after that solvent has been removed by evaporating it (i.e., after evaporating second solvent-extracted petroleum 128); 6) each representative produced oil sample; 7) each representative produced oil sample after it has been "topped" and 8) each core chip sample.

After all of the data described above has been obtained, the last step involves integrating all of the geochemical, geological, and NMR data obtained on each of the samples described above. A "topped" produced oil sample may be very similar to the producible oil that a weak organic solvent extracts from a core (after the solvent is removed by evaporating it). The composition of producible oil in a shale-oil core sample will strongly influence the composition of the petroleum extracted using a weak solvent. The composition of the bitumen in a shale-oil core sample will strongly influence the composition of the petroleum extracted using a strong organic solvent after the producible oil has been extracted by the weaker solvent. Therefore, the SRA, NMR, and geochemical data obtained on each type of sample described above can be used to estimate how much producible oil is present in each organic facies, and the key properties of the producible oil.

In the foregoing description, for purposes of explanation, numerous specific details are set forth in order to provide a thorough understanding of the disclosed embodiments. It will be apparent, however, to one skilled in the art that the disclosed embodiments may be practiced without these specific details. References to numbers without subscripts or suffixes are understood to reference all instance of subscripts and suffixes corresponding to the referenced number. Moreover, the language used in this disclosure has been principally selected for readability and instructional purposes, and may not have been selected to delineate or circumscribe the inventive subject matter. Reference in the specification to "one embodiment" or to "an embodiment" means that a particular feature, structure, or characteristic described in connection with the embodiments is included in at least one disclosed embodiment, and multiple references to "one embodiment" or "an embodiment" should not be understood as necessarily all referring to the same embodiment. It will be apparent to one skilled in the art that a method need not be practiced in the exact sequence listed in a figure or in a claim, and rather that certain actions may be performed concurrently or in a different sequence.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter. In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A method for analyzing the chemical properties of a shale-oil reservoir rock, comprising:
    extracting a core sample of a shale-oil reservoir rock using a weak solvent to form an extracted core sample and an extracted petroleum;
    drying the extracted core sample to evaporate the weak solvent;
    obtaining first data on the extracted core sample;
    extracting the extracted core sample using a strong solvent to form a twice-extracted core sample and a second solvent-extracted petroleum;
    drying the twice-extracted core sample to evaporate the strong solvent;
    obtaining second data on the twice-extracted core sample; and
    correlating the first and second data to determine producible oil quantities for the shale-oil reservoir rock.

2. The method of claim 1, wherein each solvent is an organic solvent.

3. The method of claim 1, further comprising obtaining preliminary data on the core sample before the core sample has been extracted using a solvent.

4. The method of claim 1, further comprising:
    evaporating extracted petroleum to reduce the presence of the weak solvent in the extracted petroleum; and
    evaporating second solvent-extracted petroleum to reduce the presence of the strong solvent in the second solvent-extracted petroleum.

5. The method of claim 4, further comprising:
    obtaining first petroleum data on the extracted petroleum; and
    obtaining second petroleum data on the second solvent-extracted petroleum.

6. The method of claim 5, further comprising:
    interpreting the first and second petroleum data with the first and second data to determine producible oil quantities in the shale-oil reservoir rock.

7. The method of claim 5, wherein obtaining first petroleum data on the extracted petroleum comprises determining elemental contents of the extracted petroleum, and obtaining whole-oil gas chromatographs on the extracted petroleum.

8. The method of claim 7, wherein determining the elemental contents of the extracted petroleum comprises determining the abundance of sulfur, nickel, and vanadium in the extracted petroleum.

9. The method of claim 5, wherein obtaining first petroleum data on the extracted petroleum comprises performing a saturates, aromatics, resins, and asphaltenes analysis on the extracted petroleum.

10. The method of claim 5, wherein obtaining first petroleum data on the extracted petroleum comprises performing a carbon isotopic composition analysis on the extracted petroleum.

11. The method of claim 4, further comprising filtering solids from the second solvent-extracted petroleum.

12. The method of claim 4, further comprising:
obtaining crude oil data on one or more representative crude oil samples produced from the shale-oil reservoir rock and on topped samples of that crude oil; and
interpreting the first and second petroleum data, the crude oil data, the topped oil data, and the first and second data to determine producible oil quantities for the shale-oil reservoir rock.

13. The method of claim 1, wherein the core sample is obtained by crushing and homogenizing two or more samples of facies from the shale-oil reservoir rock.

14. The method of claim 1, wherein obtaining first data on the extracted core sample comprises performing an X-ray diffraction analysis of the extracted core sample, performing a programmed pyrolysis on the extracted core sample, performing a shale property analysis on the extracted core sample, and performing a nuclear magnetic resonance imaging analysis on the extracted core sample.

15. The method of claim 1, further comprising:
extracting the twice-extracted core sample using a third solvent to form a thrice-extracted core sample and a third solvent-extracted petroleum;
drying the thrice-extracted core sample to evaporate the third solvent; and
obtaining third data on the thrice-extracted core sample,
wherein correlating the first and second data to determine producible oil quantities for the shale-oil reservoir rock comprises correlating the first, second, and third data to determine producible oil quantities for the shale-oil reservoir rock.

16. The method of claim 15, wherein the weak solvent comprises cyclohexane, the strong solvent comprises toluene, and the third solvent comprises a chloroform methanol mixture.

17. The method of claim 1, wherein the weak solvent comprises cyclohexane.

18. The method of claim 1, wherein the strong solvent comprises toluene or a chloroform methanol mixture.

19. A method for analyzing the chemical properties of a shale-oil reservoir rock, comprising:
analyzing one or more native core samples to obtain a first set of data;
homogenizing the one or more native core samples to form a homogenized sample;
analyzing the homogenized sample to obtain a second set of data;
extracting the homogenized sample using a weak solvent to form an extracted sample and an extracted petroleum;
analyzing the extracted sample to obtain a third set of data;
analyzing the extracted petroleum to obtain a fourth set of data;
correlating the first, second, third, and fourth sets of data to determine producible oil quantities for the shale-oil reservoir rock.

20. A method for analyzing the chemical properties of a reservoir rock, comprising:
extracting a core sample of a reservoir rock using a first solvent to form an extracted core sample and an extracted petroleum;
drying the extracted core sample to evaporate the first solvent;
allowing the first solvent to evaporate from the extracted petroleum;
extracting the extracted core sample using a second solvent to form a twice-extracted core sample and a second solvent-extracted petroleum;
drying the twice-extracted core sample to evaporate the strong solvent;
allowing the second solvent to evaporate from the second solvent-extracted petroleum;
correlating data obtained with each act to determine oil quantities for the reservoir rock.

* * * * *